United States Patent [19]
Bell

[11] Patent Number: 6,051,750
[45] Date of Patent: Apr. 18, 2000

[54] METHOD AND CONSTRUCT FOR PRODUCING GRAFT TISSUE FROM AN EXTRACELLULAR MATRIX

[75] Inventor: Eugene Bell, Boston, Mass.

[73] Assignee: Tissue Engineering, Inc., Boston, Mass.

[21] Appl. No.: 09/143,986

[22] Filed: Aug. 31, 1998

Related U.S. Application Data

[60] Division of application No. 08/471,535, Jun. 6, 1995, Pat. No. 5,800,537, which is a continuation-in-part of application No. 08/302,087, Sep. 6, 1994, Pat. No. 5,893,888, which is a continuation of application No. 07/926,885, Aug. 7, 1992, abandoned.

[51] Int. Cl.$^7$ ........................................................ A61F 2/02
[52] U.S. Cl. ................................................................ 623/11
[58] Field of Search ................................ 623/1, 2, 11, 12, 623/66; 424/195.1, 424

[56] References Cited

U.S. PATENT DOCUMENTS

| | | |
|---|---|---|
| 4,485,096 | 11/1984 | Bell . |
| 4,485,097 | 11/1984 | Bell . |
| 4,501,815 | 2/1985 | Reid et al. . |
| 4,505,266 | 3/1985 | Yannas et al. . |
| 4,642,292 | 2/1987 | Reid et al. . |
| 4,645,669 | 2/1987 | Reid . |
| 4,661,111 | 4/1987 | Rooslahti . |
| 4,776,853 | 10/1988 | Klement et al. . |
| 4,795,459 | 1/1989 | Jauregui . |
| 4,801,299 | 1/1989 | Brendel et al. . |
| 4,837,285 | 6/1989 | Berg et al. . |
| 4,902,508 | 2/1990 | Badylak et al. . |
| 4,917,890 | 4/1990 | McAnalley . |
| 4,935,000 | 6/1990 | Dudek . |
| 4,950,483 | 8/1990 | Ksander et al. . |
| 4,956,178 | 9/1990 | Badylak et al. . |
| 4,969,912 | 11/1990 | Kelman et al. . |
| 4,981,841 | 1/1991 | Gibson . |
| 5,024,841 | 6/1991 | Chu et al. . |
| 5,043,426 | 8/1991 | Goldstein . |
| 5,192,312 | 3/1993 | Orton . |
| 5,262,403 | 11/1993 | Nicolson et al. . |

FOREIGN PATENT DOCUMENTS 0 358 506   3/1990   European Pat. Off. .

OTHER PUBLICATIONS

Beghe, F. et al. "Lyophilized Non–denatured Type–1 Collagen(Condress) Extracted from Bovine Achilles' Tendon and Suitable for Clinical Use" *Int. J. Tiss. React.* XIV (*Suppl.*): 11–19 (1992).

Edgington, S.M. "3–D Biotech: Tissue Engineering" *Bio/technology* 10:855–860 (1992).

Githens, S. III, et al. "Ducts of the Rat Pancreas in Agarose Matrix Culture" *In Vitro* 16(9):797–808 (1980).

Woessner, J. F. Jr. "Introduction to Serial Reviews: The Extracellular Matrix" *The FASEB Journal* 7:735–736 (1993).

Nathan, C. and Sporn, M. "Cytokines in Context" *Journal of Cell Biology* 113:981–986 (1991).

Lin, C.Q. and Bissel, M.J. "Multi–faceted Regulation of Cell Differentiatio by Extracellular Matrix" *The FASEB Journal* 7:737–743 (1993).

Adams, J.C. and Watt, F.M. "Regulation of Development and Differentiation by the Extracellular Matrix" Review Article, *Development* 117:1183–1198 (1993).

*Primary Examiner*—David J. Isabella
*Attorney, Agent, or Firm*—Lahive & Cockfield, LLP; Thomas V. Smurzynski, Esq.; Nicholas P. Triano, III, Esq.

[57] ABSTRACT

Using animal tissues as starting materials, a method is described for producing extracellular matrix particulates. The invention includes an embodiment wherein the matrix particulates are applied to collagen scaffolds, which can be seeded with living cells or the particulates may alone be seeded with living cells. Further, the invention encompasses bonding the particulates to collagen foams, or collagen threads made into fabrics or to foams combined with threads. The particulates, with or without scaffolding, can be used as tissues for grafting or as model systems for research and testing. The invention also encompasses the spinning of threads on which the matrix particulates are components and the freeze drying of foams to whose surfaces the matrix particulates are attached.

7 Claims, No Drawings

METHOD AND CONSTRUCT FOR PRODUCING GRAFT TISSUE FROM AN EXTRACELLULAR MATRIX

RELATED APPLICATIONS

This application is a divisional application of Ser. No. 08/471,535, filed on Jun. 6, 1995, now U.S. Pat. No. 5,800,537. The contents of the aforementioned application are hereby incorporated by reference.

This application is a continuation-in-part application of U.S. patent application Ser. No. 08/302,087, filed on Sep. 6, 1994, now U.S. Pat. No. 5,893,888 which is a continuation of U.S. patent application Ser. No. 07/926,885, filed on Aug. 7, 1992, now abandoned, the teachings of each application are incorporated herein by reference in their entirety.

BACKGROUND OF THE INVENTION

The use of synthetic materials, such as polyester fiber (Dacron™) or polytetrafluroethylene (PTFE) (Teflon™) as implants designed to replace diseased or damaged body parts, has been extensive. These materials have however, enjoyed limited success. This has been due to the poor biocompatibility of these materials which among other problems, frequently initiate persistent inflammatory reactions. Additionally, the failure of the body to integrate these materials, because they do not break down and do not lend themselves to remodeling by tissue cells that may come into contact with them, causes further problems.

Efforts to use animal or human materials have also been unsatisfactory when these materials are crosslinked by formaldehyde or glutaraldehyde, for example. The process of generalized aldehydic crosslinking renders biomaterials sufficiently unrecognizable to tissue cells so that normal remodeling and integration are not promoted. Similarly, other types of chemical processing of animal or human biomaterials, such as extraction with detergents, or hypertonic buffers or hypotonic buffers can alter them to the degree that they are toxic to tissue cells and ineffective in promoting angiogenesis and in stimulating repair and remodeling processes needed for the conversion of an implant into a functional substitute for the tissue or organ being replaced.

A third approach has been that of reconstituting tissue and organ equivalents from structural matrix components, such as collagen, for example, that have been extracted, purified and combined with specialized cells and gelled. The process depends upon interactions between the cells and collagen filaments in the gel that the cells condense and organize. While tissue-like constructs have been fabricated and been shown to somewhat resemble their natural counterparts, they do not readily develop the matrix complexity characteristic of the actual tissues they are meant to imitate. See, for example, U.S. Pat. Nos. 4,485,096 and 4,485,097, both issued to Eugene Bell on Nov. 27, 1984.

SUMMARY OF THE INVENTION

The present invention relates to a method for producing extracellular matrix particulates constituting a scaffold to which extracellular matrix particulates are bound and a fabric having tissue extracellular matrix particulates.

A tissue source having living cells is processed to derive an extracellular matrix, whereby the living cells are disrupted to form cell remnants. The tissue source is processed to remove the cell remnants from the extracellular matrix of the tissue source without removing growth factors necessary for cell growth, morphogenesis and differentiation to form a processed extracellular matrix. The processed extracellular matrix source is fragmented to produce tissue matrix particulates. Further, the extracellular matrix particulates can be combined with a biopolymer scaffold. The scaffold with extracellular matrix particulates can be seeded with cultivated cells under such conditions that the cells adhere to the scaffold and extracellular matrix particulates.

A biopolymer scaffold consists of a fabric, which is formed of a polymer by weaving, knitting, braiding or felting threads and to which the extracellular matrix particulates are applied. If the polymer is collagen, the scaffold is crosslinked before the particulates are applied to it.

An advantage of this invention is that the formed tissues include use as skin, blood vessels, glands, periodontal prostheses and others.

DETAILED DESCRIPTION OF THE INVENTION

The above features and other details of this invention will now be more particularly described and pointed out in the claims. It will be understood that the particular embodiments of the invention are shown by way of illustration and not as limitations of the invention. The principal features of this invention can be employed in various embodiments without departing from the scope of the invention. All parts and percentages are by weight unless otherwise specified.

The present invention embodies a new method for preparing animal tissues and material derived from them as transplants designed to substitute for tissues or organs that are damaged or diseased. This is accomplished in such a way that their native complexity is preserved and thus allows them to be remodeled and integrated by the specialized cells with which they are brought into contact. In other words, because the matrix particulates of the present invention contain cell growth and differentiation stimulatory molecules, they provide the biomolecular signals needed for in vivo tissue repair or for tissue formation in vitro in a model tissue system in which cells have been seeded. In contrast to methods previously described, the method of the present invention avoids the use of harsh reagents, such as high salt, or delipidation reagents, such as butanol/ether or detergents. The use of such reagents in methods previously described is responsible for removing from the source tissue a great many factors whose presence is considered essential for stimulating repair and remodeling processes needed for the conversion of an implant into a functional substitute for the tissue or organ being replaced.

The invention includes a method of producing tissues for grafting or for use as model systems in vitro by obtaining extracellular matrix from fetal and other tissue sources; by processing it to remove associated cells without removing factors necessary for cell growth, morphogenesis and differentiation and by combining it with collagen scaffolding with or without cells to produce tissues.

A scaffold or scaffolding includes polymers, such as collagen in the form of a foam, thread, fabric or film. Also, the scaffold can be other biodegradable polymers. Further, the scaffold can be the micro particulates themselves.

To prepare the extracellular matrix, the fetuses or other animal materials can be flash-frozen at the Slaughterhouse. Fetuses are frozen in utero with the ends of the uteri tied off before freezing to insure the sterility of fetuses in their amnions. The fetuses are thawed under class 100 clean room conditions and the tissues are dissected for processing.

In one embodiment, the tissue is minced, manually and mechanically without heating to rupture the structure and reduce it to particulates of sizes no greater than about two cubic millimeters. Particles are washed in buffer to remove blood and intracellular components. Particles are then freeze-dried, cryomilled and size-sorted. The range of sizes is in the range of between about 10 and 500 μm in diameter. In another embodiment, the tissue is freeze-dried after dissection and processed on demand.

The invention also includes methods of producing extracellular matrix for tissue building which comprise the above method with the additional steps, alone or in combination, of 1) again processing the cellular tissue particulates to remove the components without removing the factors necessary for cell growth, morphogenesis and differentiation; 2) combining the particulates with collagen scaffolding, and 3) seeding the scaffold to which extracellular matrix particulates are attached with cultivated cells under such conditions that the cells adhere to or populate the scaffold.

Advanced methods of in vitro cell cultivation permit expansion of small numbers of stem cells or of differentiated cells into large cell banks. Tissue matrix vehicles that can stimulate cell division and differentiation of these specialized cells for delivery to the human recipient in the clinic are needed. The present invention can be used to bring a disease, such as diabetes, under control by engineering and implanting reconstituted tissues or composites populated by cells with the appropriate functional capacity to overcome the problems caused by absent or insufficient insulin biosynthesis or its regulated delivery. For example, particulates of the present invention can be combined in vitro with cells from the islets of Langerhans, or with undissociated islets, first to stimulate division of the glandular islet cells and second to provide transplantation vehicles in the form of pseudoislets. In another embodiment, the pseudoislets can be combined into a tissue-like structure by seeding them into collagen foams to create a coherent tissue. An example of a method for forming biopolymer foams having extracellular matrix particulates is disclosed in U.S. patent application Ser. No. 08/343,172, filed on Nov. 22, 1994, the teachings of which are herein incorporated by reference in its entirety. Further, pseudoislets may be implanted directly, for example, by using a hypodermic syringe or similar devise to deliver them to the desired site. This invention similarly may be used to treat Parkinson's disease by providing the patient with a tissue containing dopamine producing cells. For that use, nerve cells can be plated onto the particulates to allow a delivery vehicle to form. This can be useful in the repair of neural tissue defects.

The method of this invention also has broad applications in the rebuilding of damaged or aberrant body structures, such as skin, various tubular structures and skeletal structures, such as bone, tendon and ligament. The invention may also be used to create tissue scaffolds combined with extracellular matrix particulates without added cells which scaffolds, after implantation at a chosen site, are populated by contiguous or circulating cells of the host. In one embodiment, the extracellular matrix particulates can be added uniformly to the surfaces of a collagen foam cast in a required shape, a sheet or tube, for example. In another embodiment, the particulates of the present invention can be added to collagen fibers or to fabrics of collagen fibers prepared by textile methods in the shape of prostheses. For example, the particulates can be used to coat collagen threads or other bioabsorbable or biodegradable or non-biodegradable polymer threads. For example, collagen is extruded into a coagulation bath, then transferred to a bath containing absolute ethanol or acetone, or another dehydrating solution. The thread can also be subjected to dehydration by some other means, for example vacuum-drying. Before coating with extracellular matrix particulates, it is required that the collagen be crosslinked. The preferred method for crosslinking is by exposure to ultraviolet radiation as those practiced in the art are aware. An example of an apparatus and method for spinning and processing collagen fiber having extracellular matrix particulates is disclosed in U.S. patent application Ser. No. 08/333,414, filed on Nov. 2, 1994, the teachings of which are herein incorporated by reference in its entirety.

In a further embodiment, the method of the present invention is used to produce matrix particulates from fetal animal skeletal elements prior to mineralization or from demineralized animal bone. The fetal matrix particulates can be combined with osteogenic cells in bone-shaped collagenous containers to form skeletal constructs. The collagenous, external surface of the containers can be plated with a second cell type associated with periosteal tissue. In a similar manner, a composite derived from dermal matrix particulates combined with a foam, or fiber, or foam-plus-fiber sheet can be over-plated with keratinocytes to form a skin-like construct.

The cell-free tissue particulates combined with a collagen scaffold made from a collagen foam, collagen threads in fabric form or from a combination of foams and threads can be used as an implant for host cells to populate. Some freeze-dried tissues can also be used without fragmentation, but perforated before use.

The invention includes another method for producing tissues which comprises obtaining a desired tissue source having an extracellular matrix and processing as above to remove living cells without removing the growth factors necessary for cell growth and differentiation. The tissue source can be frozen or freeze-dried, then fragmented to produce tissue particulates. The tissue particulates are seeded with cultivated cells under such conditions that the cells adhere to and populate the tissue particulates. In one embodiment, the tissue particulates are seeded with cultivated cells and then packed into a preformed porous polymeric container. This method can also include the optional step of further processing the tissue particulates before they are seeded, in order to remove remaining cellular components without removing other factors necessary for cell growth and differentiation.

The invention includes another method for producing tissues which comprises obtaining a desired tissue source and processing as above to remove living cells without removing factors necessary for cell growth and differentiation. The tissue source is then processed by a method, such as freezing or freeze-drying, and fragmented to produce specific tissue particulates. In the alternative, the cells can be removed prior to fragmentation. The particulates can be applied to threads of collagen or other polymers to make coated threads, or they can be applied to fabrics made from the threads or foams. If the threads or foams or fabrics formed from the threads are collagen, they are crosslinked before adding microparticulates. The threads of the invention are coated with particulates which come from a specific tissue or from a combination of tissues. Crosslinking with ultraviolet radiation must precede the application of particulates whose biological activity would otherwise be adversely affected. These threads are then braided or woven to form fabrics or other complex constructs for implantation or for use in model systems for research and testing applications.

The invention encompasses another method of producing tissue which comprises obtaining a desired is tissue source and processing to remove living cells without removing factors necessary for cell growth and differentiation. According to this method, the tissue source can be processed by freezing or freeze-drying, but not fragmented. Instead, the tissue is processed in the form of sheets or strips. These sheets or strips can be frozen or freeze-dried, then thawed and perforated to allow cells to infiltrate the tissue. In one embodiment, the tissue sheets or strips are seeded with cultivated cells under such conditions that the cells adhere to and populate the sheets or strips. The seeded sheets or strips can be further shaped or molded to form useful graft tissue for grafting or for model systems. In another embodiment, the sheets or strips can be implanted into a host without first seeding with cultivated cells. According to this embodiment, the sheets or strips would provide a site for host cells to populate.

Fragmentation of the desired tissue can be achieved by freezing or freeze-drying, and then mechanically blending the frozen or freeze-dried tissue or mechanically crushing it between rollers. The desired tissue can also be fragmented by blending the tissue without first freezing it. An optional nuclease treatment is carried out for the purpose of digesting the nucleic acids released when the cells and cell nuclei are ruptured, which may result from the treatment of cell removal. The tissue particulates are then washed and collected by the serial steps of centrifugation, resuspension, recentrifugation and resuspension.

The invention further encompasses a method wherein the tissue particulates obtained by the above methods are layered onto a synthetic porous membrane to a thickness which allows diffusion of nutrients to all the tissue particulates. One embodiment of this method includes an additional step of bonding or fusing the tissue particulates to form a composite using a fusing agent. The type of fusing agents which can be selected are known to one skilled in the art. A collagen solution mixed with particulates and then dried or freeze-dried is an example of a fusing agent and process. Various biological glues, as known in the art, are fusing agents. In a preferred embodiment, in vitro cultivated cells are plated onto the tissue composite in a volume which just cover the composite and allow transportation of nutrients. The cells are plated under conditions that allow the cells to populate or adhere to the tissue particulates. One or more cell type can be plated onto the composite.

The invention further includes a construct which is produced by any of the above methods, including a multi-cell construct.

The tissue source can be derived from bovine, ovine, porcine or marine animal tissues, as well as from other species of vertebrates or invertebrates. The invention further includes extracellular matrices which are derived from a variety of body parts or tissues. In a preferred embodiment, extracellular matrix is derived from embryonic or fetal tissues. Embryonic and fetal tissues are advantageous because they include various biomolecular factors which are present in normal tissue at different stages of cell development. They are also initially sterile if prepared by the method described. The factors present in embryonic and fetal tissues include, for example, factors necessary for cell division, tissue morphogenesis and differentiation.

The term, "factors necessary for cell growth, morphogenesis and differentiation", includes the biomolecular factors which are present in normal tissue at different stages of embryonic and fetal development and during tissue maintenance and repair throughout life during which cell division and differentiation may occur continuously or periodically. These factors promote angiogenesis and stimulate repair and processes needed for the conversion of an implant into a functional substitute for a tissue being replaced or for a tissue being built by cells in vitro for research and testing applications.

The extracellular matrices of tissues in the body are rich in structural proteins and in growth and differentiation factors secreted by cells. The structural elements, which include collagens, glycoproteins and proteoglycans, are arrayed in a tissue specific microarchitecture. The growth and differentiation factors, which cells secrete, bind to the structural elements of the extracellular matrix and regulate cell behavior in a number of ways. For example, the extracellular matrix controls the local concentration of and the biological activity of cell secreted factors which can then stimulate the secreting cells, exerting an autocrine influence. Alternatively, the secreted factors can stimulate neighboring cells, exerting a paracrine influence. The influence, in the form of gene activation, leads to new biosynthetic products or to cell division or cell detachment from a substrate or to cell movement.

The components of the extracellular matrix itself can stimulate biosynthesis of growth factors and growth factor receptors found at the surface of cells protruding into the extracellular matrix. The extracellular matrix can also be mitogenic. The structural proteins of the matrix embody intrinsic growth factor activity. For example agrin, laminin, and thrombospondin contain epidermal growth factor (EGF) repeats. Laminin, tenacin and thrombospondin have been shown to exhibit mitogenic activity. The extracellular matrix can control cell division triggered by growth factors by regulating cell shape. Some growth and differentiation factors bind to the extracellular matrix by way of glycosaminoglycans.

Examples of factors which bind to heparin or heparin sulfate chains include epidermal growth factor, multipotential growth factor, mast cell-stimulating factor, platelet-derived growth factor, transforming growth factor-$\beta$ binds to proteoglycan core proteins and glycoproteins, such as fibronectin and thrombospondin, platelet-derived growth factor binds to osteonectin, and $\beta$-endorphin to vitronectin. Using ELISA and radio immune assay, the presence of TGF$\beta$1, 2 & 3, PDGF, FGF and IGF in various extracellular matrix tissue particulates after cryopreservation and thawing have been demonstrated. This does not suggest that others are not present; simply, assays for others have not yet been carried out. Other extracellular components, such as a proteoglycans (e.g., decorin) and collagen types I and III, have also been demonstrated.

Presently, there is no exact number of "growth factors necessary for cell growth or differentiation or tissue building" because they are continually being identified. However, one having ordinary skill in this art understands and appreciates that these growth factors in cells are attached to structural elements of the extracellular matrix including proteins, glycoproteins, proteoglycans and glycosaminoglycans. It is well understood now that the principal activities of cells are governed by signals from the extracellular matrix. The growth factors are secreted, bind to the extracellular matrix and regulate cell behavior in a number of ways. These factors include, but are not limited to, epidermal growth factor, fibroblast growth factor (basic and acidic), insulin growth factor, nerve growth-factor, mast cell-stimulating factor, platelet-derived growth factor, transforming growth factor-$\beta$, platelet-derived growth factor, scatter factor/hepatocyte growth factor, Schwann cell growth factor and pleiotrophin depending on the tissue source.

The tissue source is processed to remove cell contents without removing the growth factors and structural molecules with which they are associated in the extracellular matrix and which are necessary for tissue building by cells. The products, extracellular matrix particulates, are then used in the ways described. In a preferred embodiment, they are combined with a collagen scaffold in the form of a collagen foam or a collagen fabric of threads to constitute a prosthesis of some required shape to which cells may or may not be added. The minimally processed extracellular matrix is a tissue-specific informational component to be added to the scaffold of the prosthetic device. The invention has the advantage of employing tissue components from a non-recipient and of not being limited to autoimplantation. For in vitro use as model systems for research for testing or for other applications, cells are added to the particulate-decorated scaffolds to constitute living tissues.

An additional embodiment of using the extracellular matrix microparticulates consists of inactivating them by heating to about 56° C. for one hour. While this treatment destroys chemical biological activity, it does not degrade microarchitectural relationships of components. Active extracellular matrix components are then added to the heat-treated particulates to provide specific single or multiple instructive signals.

The connective tissue matrix and particulates derived through the above methods and combined with a shaped collagen scaffold can be seeded with selected cultured human or other cells. The reconstituted living tissue of various shapes can be used with or without the addition of supplementary growth and differentiation factors.

In a preferred embodiment, the matrix particulates are selected to match the tissue being fabricated. For is example, if a skin replacement is the objective, preferably dermal matrix would be particularized and with a scaffold, a composite with dermal cells constructed. If neural tissue replacement is the goal, preferably embryonic or fetal central nervous system connective tissue matrix would be chosen for combination with the appropriate cells to form a composite.

The processing steps of the above methods are performed in order to remove cells from the selected animal tissues, thereby producing extracellular matrix reduced to particulates. There are many methods known in the art for removing cells from tissue. The following are examples of some of these methods. These examples are not intended to be an exhaustive list, but are merely examples of some of the known methods. The choice of method and the sequence of treatments depend on the type of tissue being processed.

Various methods for removing cells from the tissue source without removing factors necessary for cell growth, morphogenesis and differentiation include scraping tissue with a blade or blade-like instrument. Alternatively, the tissue can be squeezed by rollers to remove the soft components including cells. The tissue is not fragmented while removing the cells. The cells are destroyed but not all of the cellular components are necessarily removed even though the cells are ruptured. Although a blade, rollers or enzymes can macerate the tissue, the fragmentation step can be separate. For instance, the tissue is squeezed and washed to remove cell fragments. These methods can also be employed to remove remaining cytoplasmic and nuclear components in tissue particulates produced by fragmentation of the tissue source.

The freezing and/or freeze-drying, and fragmentation steps are done to produce particulates and to further free the tissue of undesirable components. Since cells are fractured by freezing and contents are released, the tissue can also be treated with enzymes, particularly nucleases. Additionally, the tissue can be passed through a freeze-thaw, or freeze-dry-thaw cycle in order to disrupt the living cells to form cell remnants which can be washed out of tissues leaving essentially extracellular matrix. Methods for sterilizing processed tissues are known to one skilled in the art and include contacting the tissue with a peracetic acid solution, preferably about a 0.5% solution, and washing the tissue in a sterile buffer, preferably sterile phosphate buffered saline. The tissue can then be freeze-dried by being brought to the temperature of liquid nitrogen, then fragmented under sterile conditions.

Fetal tissue taken from sterile fetuses contained in their intact amnions can be kept sterile under clean room conditions. Fragmentation at low temperature can be carried out in many ways known to those skilled in the art; manual shearing with knives or scissors is one. Fragmentation methods could include a shearing device, such as a mechanical blender, or a mechanical crusher to yield particulates. Particulates are further reduced by cryomilling, after which they are screen-sized. In a preferred embodiment, the particulates fall in a range between about 10 and 500 micrometers in diameter; for some applications the particulates can be as small as about 5–10 microns. Depending on the starting tissue type, further nuclease cleaning and washes followed by centrifugation and resuspension in fresh phosphate buffered saline can be carried out in an effort to minimize the presence of components which could be immunogenic.

In another embodiment, the tissues can be dehydrated chemically with acetone, absolute alcohol or hydrophilic polymers, such as carbowax, and then fragmented.

After the particulates are prepared, they are seeded with cells. Preferably, one can use human cells for populating the matrix, but the invention is not limited to human cells. In one embodiment, the seeding process is carried out by rehydrating the matrix particulates using tissue culture medium, with or without growth and differentiation supplements added, and allowing the particulates to swell to equilibrium with their fluid environment before applying cells to them.

In another embodiment, the matrix particulates are populated with cells of one, or more than one phenotype in a bioreactor, spinner flask or other similar device to expand cell number. The number of cells used and the time of residence in the device depends on cell attachment time and the desired degree of coverage of the particulate by the cells. These parameters vary depending on the type of cell used and the cell density required for the final product. The particular parameters for each cell type will be apparent to one skilled in the art. In a preferred embodiment, the starting cell density is in the range of between about $0.5 \times 10^4$ and $10^6$ cells per milliliter. In another embodiment, the prepared particulates can be combined with collagen scaffolds in the form of foams or fiber based textiles of shapes appropriate for prostheses or model systems for research or testing applications.

The matrix particulates, with or without cells, can be layered onto a synthetic porous membrane. Examples of a synthetic porous membrane, for illustrative purpose only and not to limit the invention in any way, include membranes made of polycarbonate, for example, in a transwell arrangement, or onto a bioabsorbable polymer, such as a porous collagen foam that lines a mold having a porous membrane for a bottom to hold the collagen foam and permit passage of medium from below. The membrane may also be made of other bioabsorbable polymers, such as poly-l-lactate or of thermosetting polymers. In one embodiment, the particulates are layered in a single layer. Also, in one embodiment, the layer may vary between about 0.2 and 3 millimeters in thickness.

A further embodiment includes the use of multiple cell types, one type plated in a collagen foam to which matrix particulates are applied or on collagen threads which have been decorated with adhering matrix microparticulates and another cell type plated on the lower or upper surface of the scaffold.

Further, the invention encompasses the embodiment where the cell-laden particulates are packaged in a pre-formed porous collagen or other polymeric container of any desired shape. Additionally, the invention includes the use of concentric tubes of differing radii where, in a preferred embodiment, the radii would differ by only about one millimeter or less. It is also envisioned that the other shapes can be used as well.

The containers can be reinforced by struts or other means to maintain uniform thickness. The frequency of the struts is preferably in the range of between about one and ten per square millimeter. The container can be made of a collagen sheet with pores that are too small to allow particulates to escape. In a preferred embodiment, the pores measure in the range of between about ten and sixty microns. After introduction of particulates through an end opening, the container can be sealed by suturing or other means.

In another embodiment, the tissue particulates are applied to threads suitable for weaving or braiding. If the threads are of collagen, they are crosslinked before addition of matrix particulates which adhere to the threads when applied after the crosslinked threads are hydrated. The threads can be woven into fabrics or other complex constructs for implantation. The matrix particulates can be applied to the fabric after they are braided, woven, etc. The braided or woven fabrics provide a scaffold with applied matrix particulates for host cells to adhere to. In addition, the thread or fabrics produced from the threads can be seeded with cells in vitro, as above, and then transplanted into the appropriate site in the host.

In another form, a tissue can be constituted from a collagen foam to whose surfaces the particulates are applied. After a foam is formed by freeze-drying a volume of collagen in solution, the foam is crosslinked using ultraviolet radiation, a procedure known to those practiced in the art.

The foam is then filled with a collagen solution containing the extracellular matrix particulates and freeze-dried again, but not crosslinked. The result is that the surfaces of the foam are coated with the matrix particulates. The polymer used for producing the threads can be either bioabsorbable or non-bioabsorbable. In a preferred embodiment, the polymer is collagen. After extrusion, the threads of this invention are coagulated and dehydrated, for example, in a bath containing absolute alcohol, carbowax or acetone. The threads can then be dried and spooled, for example, by pulling the moving thread over more rollers, stretching and drying it and then winding it onto spools.

Exemplification I

For example, to reconstitute a skin substitute, a sheet of collagen foam enclosing a collagen thread fabric reinforcement at one of its surfaces is crosslinked with ultraviolet light and filled with a solution of collagen at 1.0 $\mu$g/ml containing 2 mg/ml microparticulates derived from near-term fetal derris. The foregoing combination is freeze-dried over a 60-hour period so that all surfaces of the collagen scaffolds are coated with microparticulates.

The resulting biologically active scaffold is seeded with cultivated dermal fibroblasts at $10^5$ cells/ml introduced into the foam side of the sheet. The threaded fabric side is plated with cultivated keratinocytes at $10^6$ cells/ml. The cell-seeded scaffolds are incubated in a 10% $CO_2$ incubator for 21 days to produce a differentiated skin prosthesis.

Exemplification II

An alternative includes of using a double-density foam sheet bonded to the single density foam at one surface of the single density foam instead of incorporating the collagen thread fabric as in Example 1. The double-density foam is produced by hydrating a crosslinked single-density foam and allowing it to dry at a temperature not greater than about 37° C. The sheet of double-density foam is positioned on the lower surface of a rectangular mold the size of the finished skin product. The double-density mold is hydrated and the mold is filled with a collagen solution of 5 mg/ml and freeze-dried. The single-density foam now fused to the double-density foam is crosslinked and dermis-specific extracellular particulates are added to the scaffold as described in Example 1. Cultivated dermal fibroblasts are seeded into the single-density foam and cultivated keratinocytes are seeded onto the double-density foam. The skin prosthesis is incubated as described in Example 1.

Exemplification III

To reconstitute an endocrine pancreas equivalent at least three organs can be used. The first is the pancreas itself, which would provide the tissue specificity of the matrix. The second is the duodenum or jejunum of the gut, and the third is the skin.

The organs are packed on ice in sterile containers immediately after animal slaughter and transported to the laboratory. The pancreas is treated using the protocol for islet removal, that is, the pancreatic duct is cannulated and Hank's solution containing 2 mg/ml collagenase (Type X, Sigma) and 2% fetal calf serum is injected. In addition, the two arteries that supply the pancreas, the celiac and the superior mesenteric, are similarly perfused with a collagenase solution containing heparin to remove endothelium from the circulatory tree of the gland. Adequate cleaning of the pancreas may require heparinizing animals before slaughter. A compression device is used to gently knead the organ as it is perfused and reperfused in a sterile chamber in the cold.

In the course of recirculation, the collagenase solution is gradually diluted. A fibrous network of ducts and vessels remains after collagenase digestion. After washing in phosphate buffered saline, the fibrous material is freeze-dried, sheared in the cold and cryomilled.

The objective of the freezing and fracturing procedure is to provide matrix particulates of between about 50 and 100 $\mu$m in diameter. The size of the particulates is also determined by the maximum allowable thickness of a tissue graft made to a host. The thickness must be consistent with survival after implantation in vivo. A collagen foam is a preferred vehicle for transplanting islets or pseudoislets because of its porosity, which include microcompartments of sizes suitable for housing islets and because it is rapidly vascularized. The goal is to produce particulates of relatively uniform size from the frozen tissue by a mechanical process that does not melt the material by frictional heating. Blending, grinding, crushing, and/or percussion in the cold at −30° C. or below are methods which can be used.

The particulates are then combined into aggregates with small clusters of cultivated cells, or are used as microbeads in a cell bioreactor in which cells from islet cell cultures are seeded. The cells attach to surfaces of the matrix microbeads in the bioreactor. The last mentioned strategy is useful as a means of expanding islet cell cultures; it can also serve as a means for constituting pseudo-islets.

The second example of an organ processed for its matrix is the jejunum or duodenum which is mechanically scraped after opening. As described in U.S. Pat. No. 4,902,508, issued to Badylak et al. on Feb. 20, 1990, the stratum compactum, about 100 μm thick, lying between luminal layers on one side and the muscular layers on the other, is delaminated from them, leaving an acellular collagenous connective tissue. The washed stratum compactum is particularized after freeze-drying, as described above.

Similarly, the third organ, skin, is stripped of epidermis and underlying adipose material and the dermis is sectioned into 100–200 μm thick sheets parallel to the dermal surface with a dermatome. It is then freeze-dried, particularized and washed in preparation for combination with cells or transplantation. Alternatively, the sheets derived from the jejunum and the dermis can be made porous or perforated with a meshing machine or similar device so that they can be seeded with cells or pseudo-islets or both.

Tissue can be formed by combining cells with foams, threads, or foams and threads to which generic or tissue-specific extracellular particulates have been applied. Such tissues can be in the form of prostheses for grafting or model systems for use in basic and applied research and for testing and diagnostic purposes. The tissues can be made to fit into transwell chambers, such as those produced by suppliers of tissue culture ware.

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. A method for producing a particulate-coated polymer thread for use as a tissue for grafting, which comprises the steps of:
   a) processing a tissue source having an extracellular matrix and living cells, whereby said living cells are disrupted to form cell remnants;
   b) processing the tissue source to remove the cell remnants from the extracellular matrix without removing growth factors necessary for cell growth and tissue development to form processed extracellular matrix;
   c) fragmenting the processed tissue source to form extracellular matrix particulates;
   d) processing a polymer so as to form a polymer thread; and
   e) coating the polymer thread with extracellular matrix particulates, thereby producing the particulate-coated polymer thread.

2. The method of claim 1 wherein the polymer is bioabsorbable.

3. A fabric formed by weaving, knitting, braiding or felting threads of claim 1 which are crosslinked and coated with extracellular matrix particulates.

4. The fabric of claim 3 wherein the polymer is collagen.

5. A fabric formed by weaving, knitting, braiding or felting threads of claim 1 which are coated with extracellular matrix particulates.

6. A method for producing a particulate-coated polymer fabric from thread for use as a tissue for grafting, which comprises the steps of:
   a) processing a tissue source having an extracellular matrix and living cells, whereby said living cells are disrupted to form cell remnants;
   b) processing the tissue source to remove the cell remnants from the extracellular matrix without removing growth factors necessary for cell growth and tissue development to form processed extracellular matrix;
   c) fragmenting the processed tissue source to form extracellular matrix particulates;
   d) processing a polymer so as to form a polymer fabric; and
   e) coating the polymer fabric with extracellular matrix particulates, thereby producing the particulate-coated polymer fabric.

7. A method for producing a particulate-coated polymer thread for use in in vitro model systems, which comprises the steps of:
   a) processing a tissue source having an extracellular matrix and living cells, whereby said living cells are disrupted to form cell remnants;
   b) processing the tissue source to remove the cell remnants from the extracellular matrix without removing growth factors necessary for cell growth and tissue development to form processed extracellular matrix;
   c) fragmenting the processed tissue source to form extracellular matrix particulates;
   d) processing a polymer so as to form a polymer thread; and
   e) coating the polymer thread with extracellular matrix particulates, thereby producing the particulate-coated polymer thread for use in in vitro model systems.

* * * * *